(12) United States Patent
Zhang et al.

(10) Patent No.: US 10,624,575 B2
(45) Date of Patent: Apr. 21, 2020

(54) MONITORING SLEEP USING MICROACTIVITY STATES

(71) Applicant: Anhui Huami Information Technology Co., Ltd., Hefei, Anhui (CN)

(72) Inventors: Feifei Zhang, Hefei (CN); Xiaoming Ren, Hefei (CN)

(73) Assignee: Anhui Huami Information Technology Co., Ltd., Hefei, Anhui (CN)

( * ) Notice: Subject to any disclaimer, the term of this patent is extended or adjusted under 35 U.S.C. 154(b) by 269 days.

(21) Appl. No.: 15/497,623

(22) Filed: Apr. 26, 2017

(65) Prior Publication Data

US 2017/0224275 A1 Aug. 10, 2017

Related U.S. Application Data

(63) Continuation-in-part of application No. PCT/CT2016/109624, filed on Dec. 13, 2016.

(30) Foreign Application Priority Data

Dec. 14, 2015 (CN) .......................... 2015 1 0939058

(51) Int. Cl.
*A61B 5/00* (2006.01)
*A61B 5/11* (2006.01)
*G16H 50/20* (2018.01)

(52) U.S. Cl.
CPC .............. *A61B 5/4815* (2013.01); *A61B 5/11* (2013.01); *A61B 5/1118* (2013.01);
(Continued)

(58) Field of Classification Search
CPC ... A61B 5/4815; A61B 5/4806; A61B 5/4809; A61B 5/4812; A61B 5/11; A61B 5/1118;
(Continued)

(56) References Cited

U.S. PATENT DOCUMENTS

2010/0145234 A1 6/2010 Jang et al.
2014/0088378 A1* 3/2014 Muzet ................ A61B 5/02125
600/301

(Continued)

FOREIGN PATENT DOCUMENTS

CN 103263260 A 8/2013
CN 103717125 A 4/2014

(Continued)

*Primary Examiner* — Matthew Kremer
*Assistant Examiner* — Avery M Foley
(74) *Attorney, Agent, or Firm* — Young Basile Hanlon & MacFarlane, P.C.

(57) ABSTRACT

A method, a wearable device, and an apparatus for monitoring sleep of a user are provided. The method includes: determining an activity amount of a user based on multi-axial acceleration data received by the wearable device in a time period, in which the multi-axial acceleration data includes acceleration data in multiple axes; if the activity amount is smaller than a first threshold, determining a microactivity feature value using the multi-axial acceleration data and predetermined weights; and determining a microactivity state for the user in the time period based on the microactivity feature value, in which the activity amount of the user is substantially zero in the microactivity state.

18 Claims, 14 Drawing Sheets

(52) U.S. Cl.
CPC .......... *A61B 5/1121* (2013.01); *A61B 5/4809* (2013.01); *A61B 5/7264* (2013.01); *G16H 50/20* (2018.01); *A61B 2562/0219* (2013.01)

(58) Field of Classification Search
CPC ................ A61B 5/1121; A61B 5/7264; A61B 2562/0219; G16H 50/20; G06F 19/00
See application file for complete search history.

(56) References Cited

U.S. PATENT DOCUMENTS

| | | | | |
|---|---|---|---|---|
| 2014/0278229 | A1* | 9/2014 | Hong ..................... | A63B 71/06 702/160 |
| 2015/0073283 | A1* | 3/2015 | Van Vugt ............... | A61B 5/113 600/476 |
| 2016/0007934 | A1* | 1/2016 | Arnold ................. | A61B 5/1123 600/595 |
| 2016/0144174 | A1* | 5/2016 | Ferree .................. | A61N 1/0476 600/595 |
| 2016/0213308 | A1* | 7/2016 | Proud .................. | A61B 5/1118 |
| 2017/0112433 | A1* | 4/2017 | Pugh ........................ | G02C 7/04 |
| 2017/0347948 | A1* | 12/2017 | Thein ................. | A61B 5/02405 |

FOREIGN PATENT DOCUMENTS

| | | | |
|---|---|---|---|
| CN | 103767710 | A | 5/2014 |
| CN | 104706318 | A | 6/2015 |
| CN | 105559751 | A | 5/2016 |
| JP | 2004089267 | A | 3/2004 |

\* cited by examiner

0
MONITORING SLEEP USING MICROACTIVITY STATES

CROSS-REFERENCE TO RELATED APPLICATION(S)

This application is a continuation-in-part of International Application No. PCT/CN2016/109624, filed on Dec. 13, 2016, which claims priority to Chinese Patent Application No. 201510939058.7, filed on Dec. 14, 2015, the contents of both of which are hereby incorporated by reference in their entireties.

TECHNICAL FIELD

This disclosure relates to methods, apparatuses and wearable devices for monitoring sleep of a user using microactivity states.

BACKGROUND

Sleep quality relates to health of individuals. A wearable device can be used to record activity amount of a user to determine a sleep state of the user, and evaluate sleep quality of the user using the sleep state. Some microactivities of the user before or after sleep (e.g., reading, using a cell phone, etc.) are similar to those in the sleep state. Although an activity amount can be used to determine the sleep state, the microactivities of the user often cannot be accurately recognized, which can affect monitoring the sleep quality of the user.

SUMMARY

Disclosed herein are implementations of a technical solution that can reduce interference in monitoring sleep quality from microactivities before bed or after waking up.

In an aspect, a method for monitoring sleep of a user using a wearable device is provided. The method includes: determining an activity amount of a user based on multi-axial acceleration data received by the wearable device in a time period, wherein the multi-axial acceleration data comprises acceleration data in multiple axes, based on a determination that the activity amount is smaller than a first threshold, determining a microactivity feature value using the multi-axial acceleration data and predetermined weights, and determining a microactivity state for the user in the time period based on the microactivity feature value, wherein the activity amount of the user is substantially zero in the microactivity state.

In another aspect, an apparatus for monitoring sleep of a user is provided. The apparatus includes a processor and a memory. The memory is configured to store instructions which when executed by the processor become operational with the processor to determine an activity amount of a user based on multi-axial acceleration data received by a wearable device in a time period, wherein the multi-axial acceleration data comprises acceleration data in multiple axes and the apparatus comprises the wearable device, based on a determination that the activity amount is smaller than a first threshold, determine a microactivity feature value using the multi-axial acceleration data and predetermined weights, and determine a microactivity state for the user in the time period based on the microactivity feature value, wherein the activity amount of the user is substantially zero in the microactivity state.

In another aspect, a wearable device for monitoring sleep of a user is provided. The wearable device includes an accelerometer having multiple axes, a processor, and a memory. The memory is configured to store instructions which when executed by the processor become operational with the processor to determine an activity amount of a user based on acceleration data in the multiple axes received by the accelerometer in a time period, based on a determination that the activity amount is smaller than a first threshold, determine a microactivity feature value using the acceleration data and predetermined weights, and determine a microactivity state for the user in the time period based on the microactivity feature value, wherein the activity amount of the user is substantially zero in the microactivity state, and wherein the user is in the microactivity state and a sleep state when the microactivity feature value is greater than a second threshold and smaller than a third threshold, the user is not wearing the wearable device when the microactivity feature value is smaller than the second threshold, and the user is in the microactivity state and a waking state when the microactivity feature value is greater than the third threshold.

BRIEF DESCRIPTION OF THE DRAWINGS

The disclosure is best understood from the following detailed description when read in conjunction with the accompanying drawings. It will be apparent that the drawings in the following description are merely examples of this disclosure, and that other drawings can be obtained from the drawings without creative work. It is emphasized that, according to common practice, the various features of the drawings are not to-scale. On the contrary, the dimensions of the various features are arbitrarily expanded or reduced for clarity.

DETAILED DESCRIPTION

The technical solution in implementations of this disclosure will be described in detail below with reference to the accompanying drawings of examples of this disclosure. It is obvious that the described examples are merely part and not all of this disclosure. Based on the examples described herein, all other examples that are available without creative work are in the scope of this disclosure.

By accurately determining microactivity states of a user, microactivities of the user before or after sleep (e.g., reading, using mobile phones) can be distinguished from microactivities of the user in a sleep state. In this way, by monitoring the microactivity states of the user, the sleep state of the user can be determined more accurately, and reliability of monitoring sleep quality of the user can be improved.

Figure 1A:
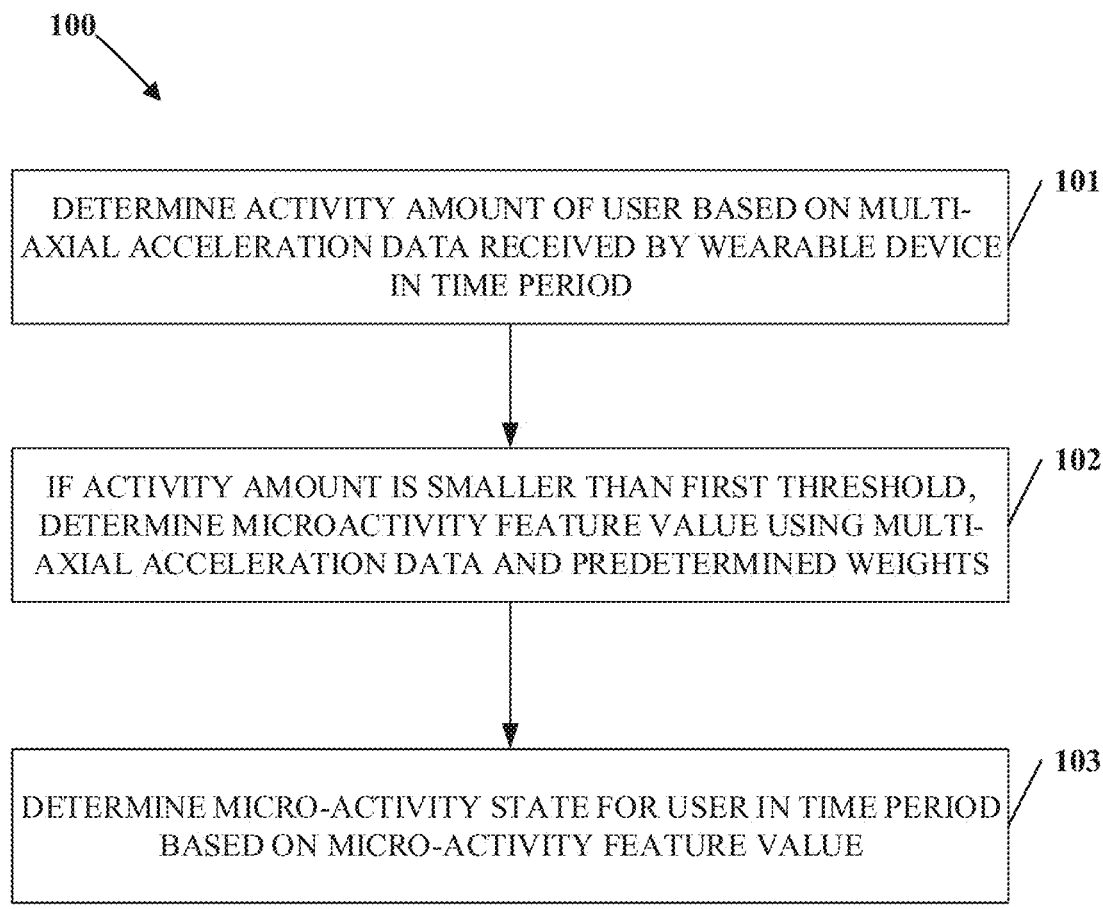
FIG. 1A is a flowchart of an example process of a method for monitoring a microactivity state according to an implementation of this disclosure.
Figure 1B:
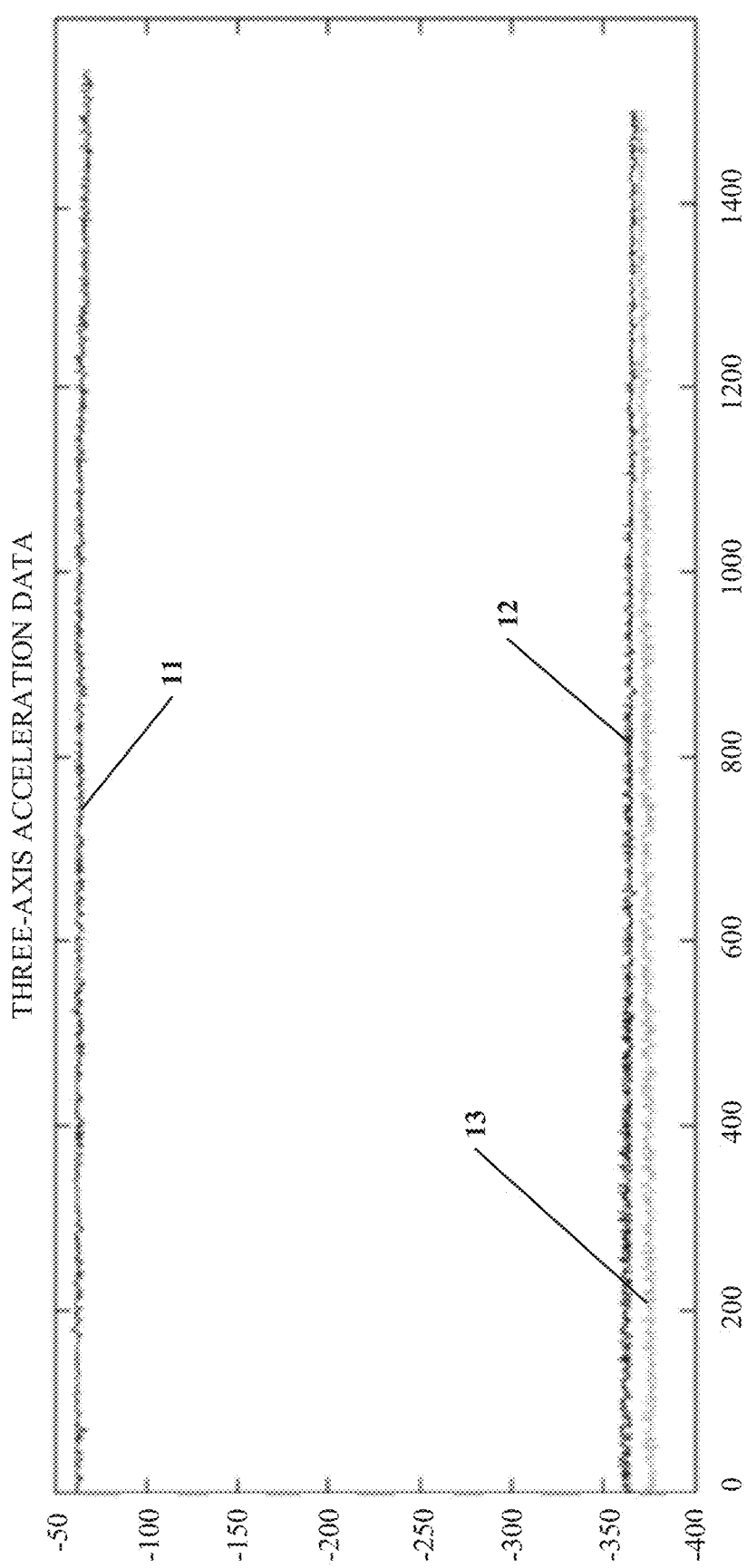
FIG. 1B is a diagram of example acceleration data received in real time when a user is in a waking state.
Figure 1C:
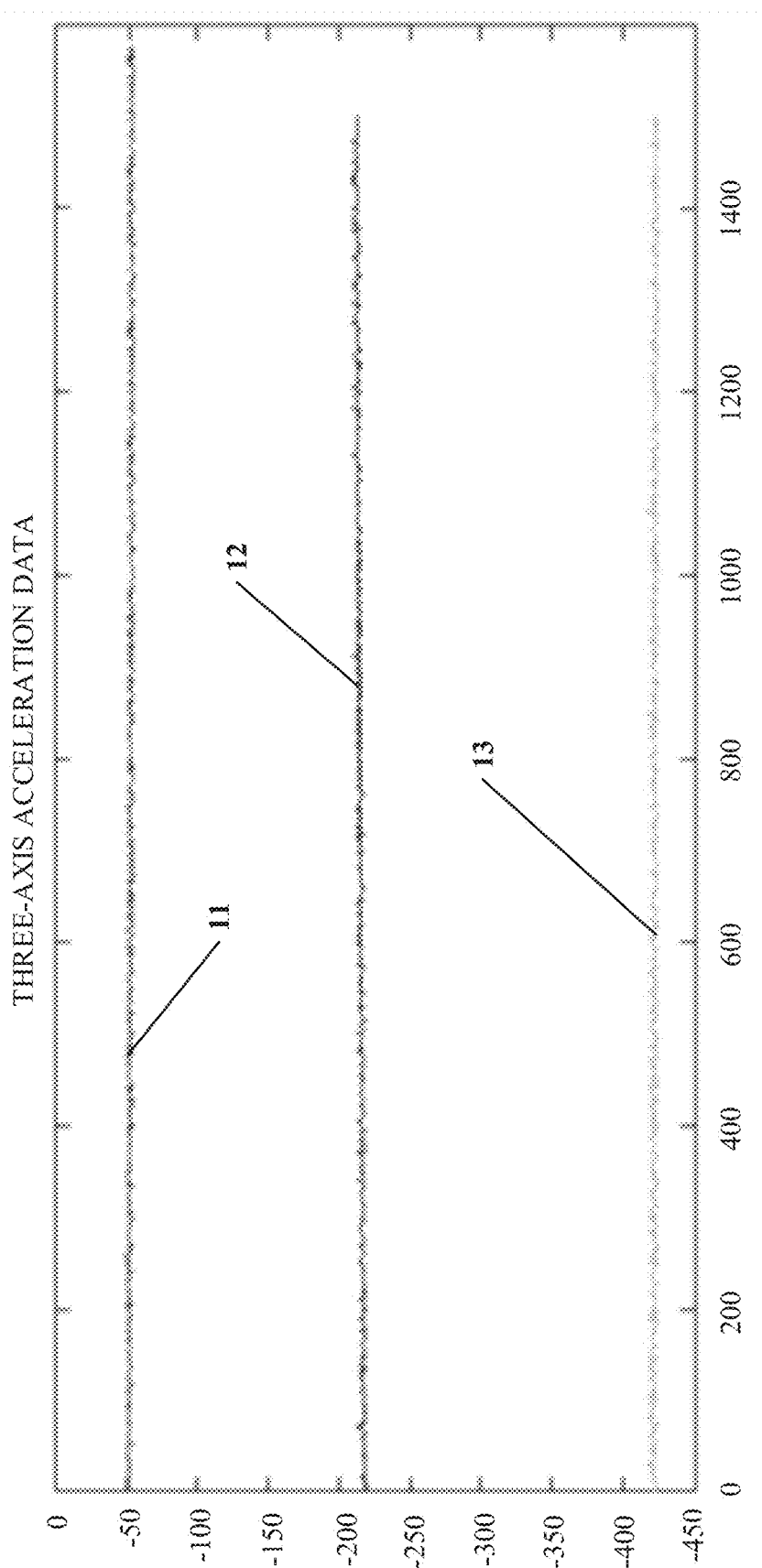
FIG. 1C is a diagram of example acceleration data received in real time when a user is in a sleep state.
Figure 1D:
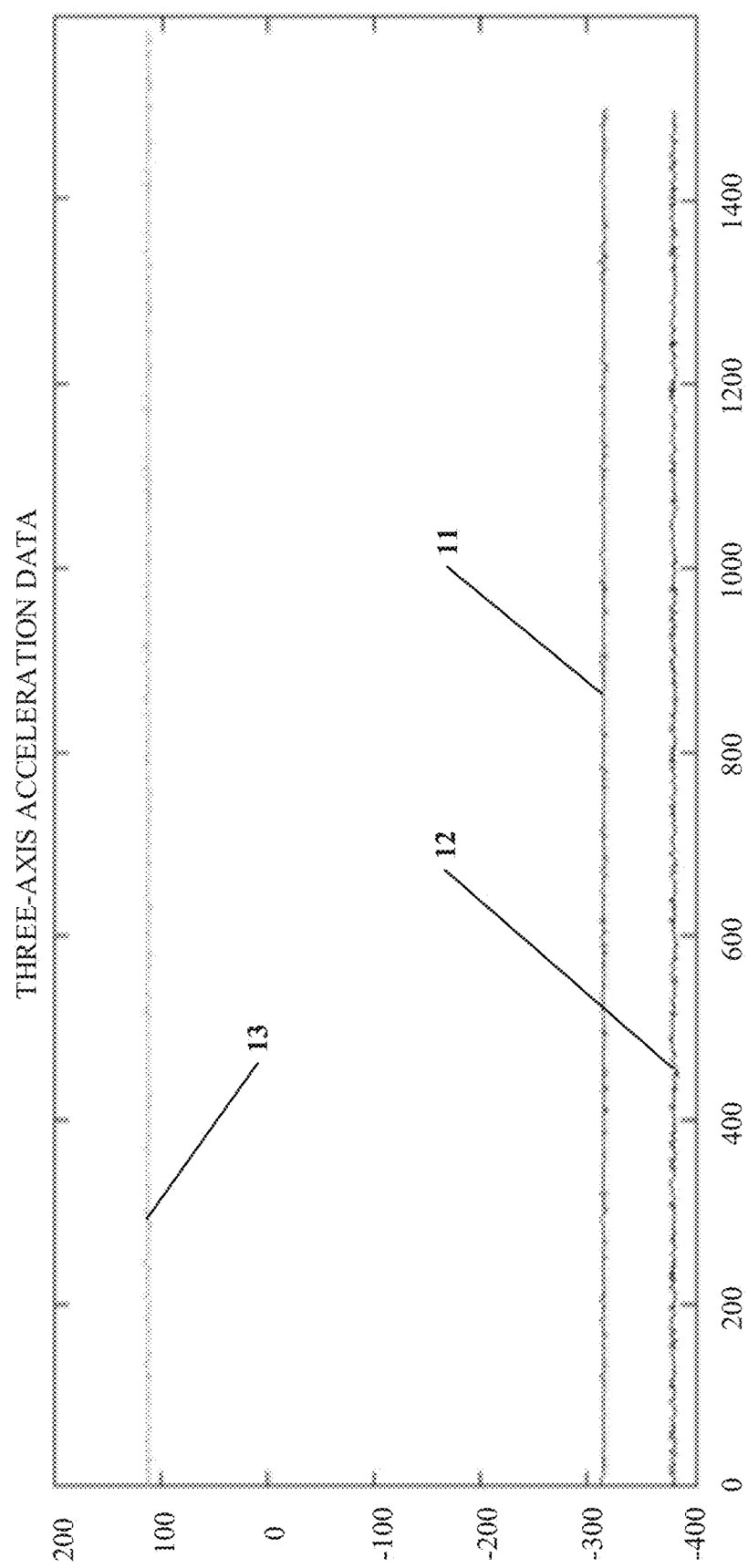
FIG. 1D is a diagram of example acceleration data received in real time when a user is not wearing a wearable device.
Figure 1E:
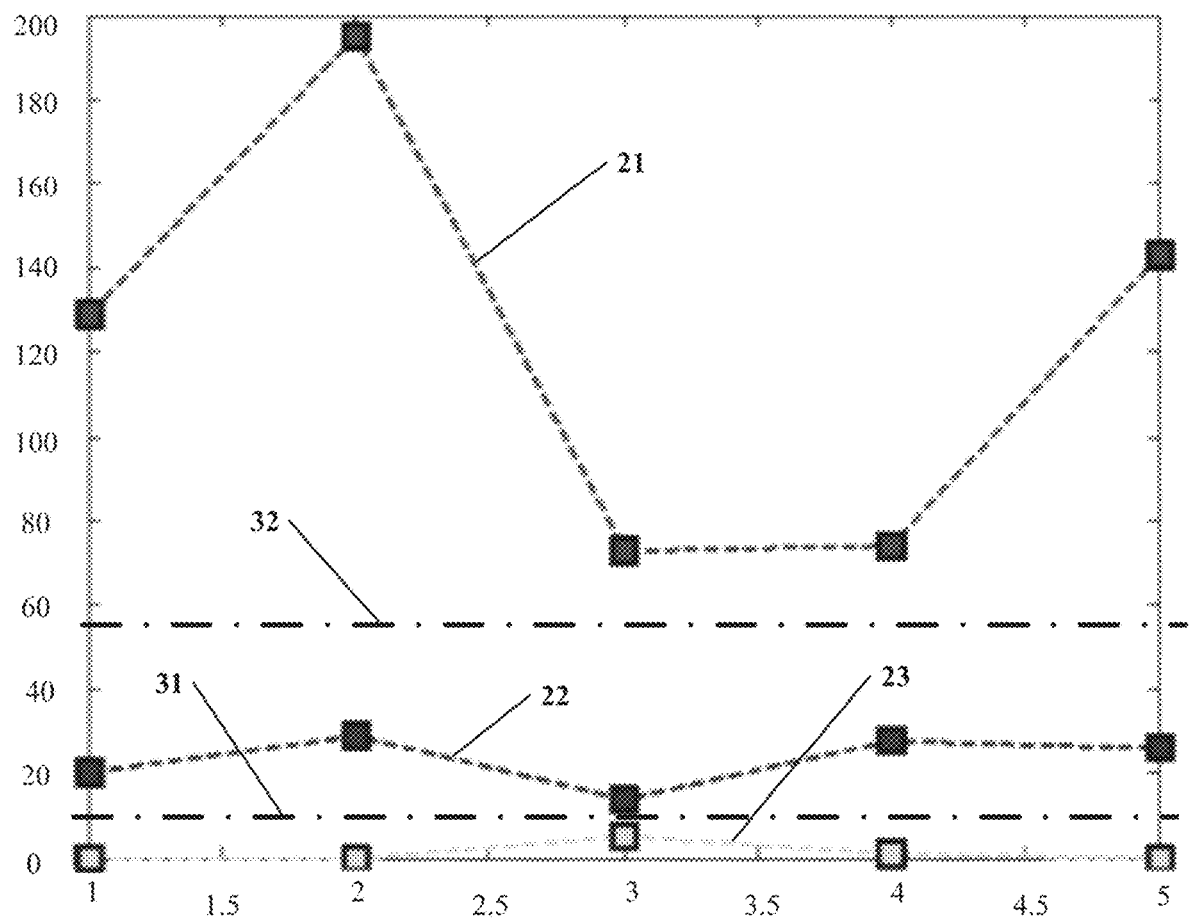
FIG. 1E is a diagram of example distribution of microactivity feature values when a user is in a waking state, a sleep state, and not wearing a wearable device.

FIG. 1A is a flowchart of an example process 100 of a method for monitoring a microactivity state according to an implementation of this disclosure. FIG. 1B is a diagram of example acceleration data received in real time when a user is in a waking state. FIG. 1C is a diagram of example acceleration data received in real time when a user is in a sleep state. FIG. 1D is a diagram of example acceleration data received in real time when a user is not wearing a wearable device. FIG. 1E is a diagram of example distribution of microactivity feature values when a user is in a waking state, a sleep state, and a state not wearing a wearable device. As shown in FIG. 1A, the process 100 can include the following operations.

At operation 101, an activity amount of a user is determined based on multi-axial acceleration data received in a set time period. The multi-axial acceleration data can be received by a wearable device. The multi-axial acceleration data can include acceleration data in multiple axial directions.

The wearable device in this disclosure can include any apparatus that can be worn at a portion of a human body, such as a wristband, a watch, a ring, a necklace, a clip, a waistband, eyewear, or a head-mounted display. Alternatively, the wearable device in this disclosure can be another portable apparatus configured to travel with but not be worn by an individual, such as a key fob.

In an implementation, the set time period can be a set time interval (e.g., every minute or every ten seconds or any other set time interval). The multi-axial acceleration data can be acceleration data received by an accelerometer of two or more axials. The term "receive" used herein can refer to receiving, inputting, acquiring, retrieving, obtaining, reading, accessing, collecting, or any action in any manner for inputting information or data. The accelerometer can be in a wearable device worn by the user.

As shown in FIGS. 1B-1D, horizontal axes represent sampling points. For example, a "200" on a horizontal axis represents a $200^{th}$ sampling point. Vertical axes represent a magnitude of the acceleration data. In an implementation, the accelerometer can be a three-axis accelerometer and the acceleration data is received by 1500 sampling points per minute. In FIGS. 1B-1D, label 11 denotes acceleration data received by the three-axis accelerometer in the x-axis direction. Label 12 denotes acceleration data received by the three-axis accelerometer in the y-axis direction. Label 13 denotes acceleration data received by the three-axis accelerometer in the z-axis direction. As shown in FIGS. 1B-1D, when the user is in a waking state, a sleep state, and not wearing the wearable device (referred to a "non-wearing state"), magnitudes of the acceleration data in x-, y-, and z-direction are relatively stable. Therefore, it can be difficult to directly distinguish the above three states based on the acceleration data, and the monitoring of the sleep state can be interfered by the waking state or the non-wearing state.

Figure 4A:
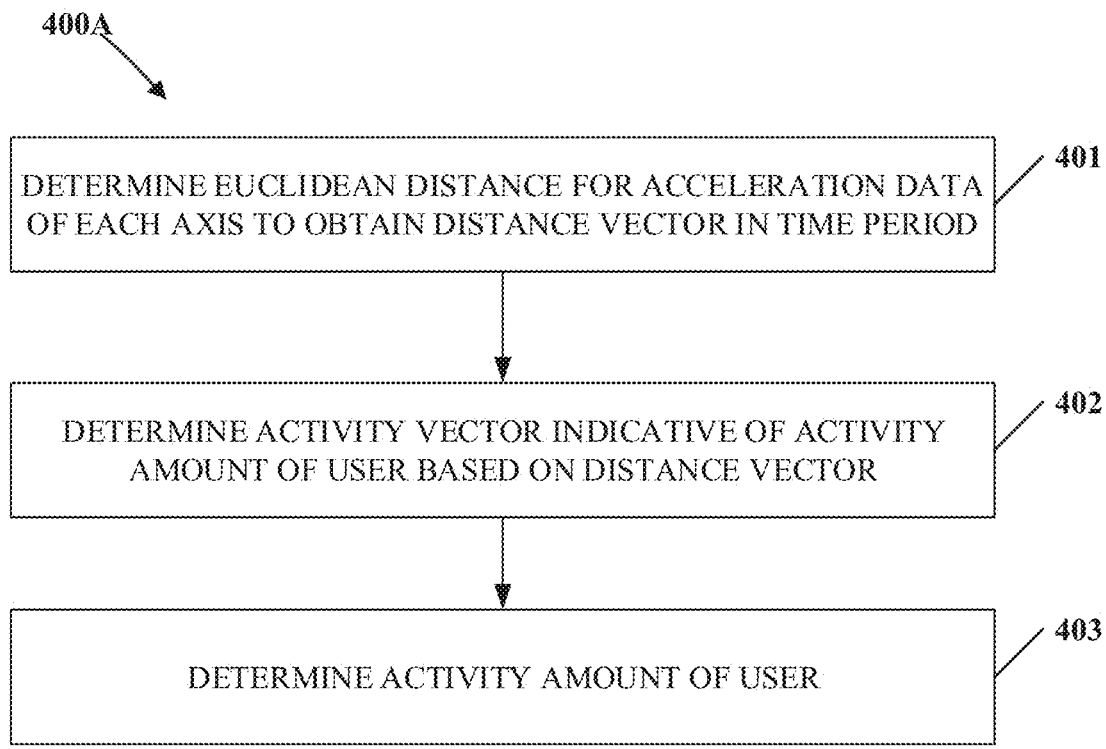
FIG. 4A is a flowchart of an example process of a method for determining an activity amount of a user according to an implementation of this disclosure.

To distinguish the three states, the multi-axial acceleration data can be converted to a corresponding activity amount to determine a microactivity state for the user. For example, the activity amount can be obtained using, such as, a Euclidean distance, a translation (or a shifting), a difference, a sum, or an average value of the acceleration data. FIG. 4A describes a specific example of determining the activity amount for the user.

At operation 102, if the activity amount is smaller than a first preset threshold, a microactivity feature value can be determined using the multi-axial acceleration data and predetermined weights. For example, microactivity feature value can be determined using (e.g., summing) axial feature values. For each axial direction of the multiple axial directions, an axial feature value can be determined based on the multi-axial acceleration data and the predetermined weights. The first preset threshold can be a positive number greater than zero. For example, for the three-axis accelerometer, three axial feature values in x-, y-, and z-direction can be determined based on the multi-axial acceleration data of the three-axis accelerometer, and the microactivity feature value can be determined based on the three axial feature values in x-, y-, and z-direction.

Because the activity amount of the user in a microactivity state is substantially close to zero, the first preset threshold can be set to a relatively small positive number to distinguish between an activity amount of the user in the microactivity state and an activity amount of the user in a normal-activity state. In an implementation, the axial feature values can be obtained by a process described in FIG. 2.

In an implementation, the axial feature values in the multiple axial directions can be summed to obtain the microactivity feature value in the set time period. For example, for the three-axis accelerometer, the axial feature values in x-, y-, and z-direction as shown in FIGS. 1B-1D can be summed to obtain the microactivity feature value.

In an implementation, if the activity amount is greater than or equal to the first preset threshold, the user can be determined as in a non-sleep state (e.g., a waking state, a moving state, or any other normal-activity state).

In some implementations, before operation 103, a microactivity feature value is determined for the set time period based on the axial feature value for each axial direction. Based on the microactivity feature value, a microactivity state can be determined.

At operation 103, a microactivity state is determined for the user in the set time period based on the microactivity feature value.

In an implementation, by processing the acceleration data in accordance with the above operations, the microactivity feature value can have different distribution features under different microactivity states. For example, as shown in FIG. 1E, label 21 denotes a distribution of microactivity feature values of the user in the waking state, label 22 denotes a distribution of microactivity feature values of the user in the sleep state, label 23 denotes a distribution of microactivity feature values of the user in the non-wearing state. As can be seen from FIG. 1E, the above three states can be accurately distinguished based on the distributions of the microactivity feature values.

As described above, by the operations 101-103, the microactivity state of the user can be relatively accurately determined, and the microactivities of the user before or after sleep (e.g., reading, or using mobile phones) can be distinguished from the microactivities of the user in the sleep state. In this way, by monitoring the microactivity states of a user, the sleep state of the user can be determined more accurately, and the reliability of monitoring sleep quality of the user can be effectively improved.

Figure 2:
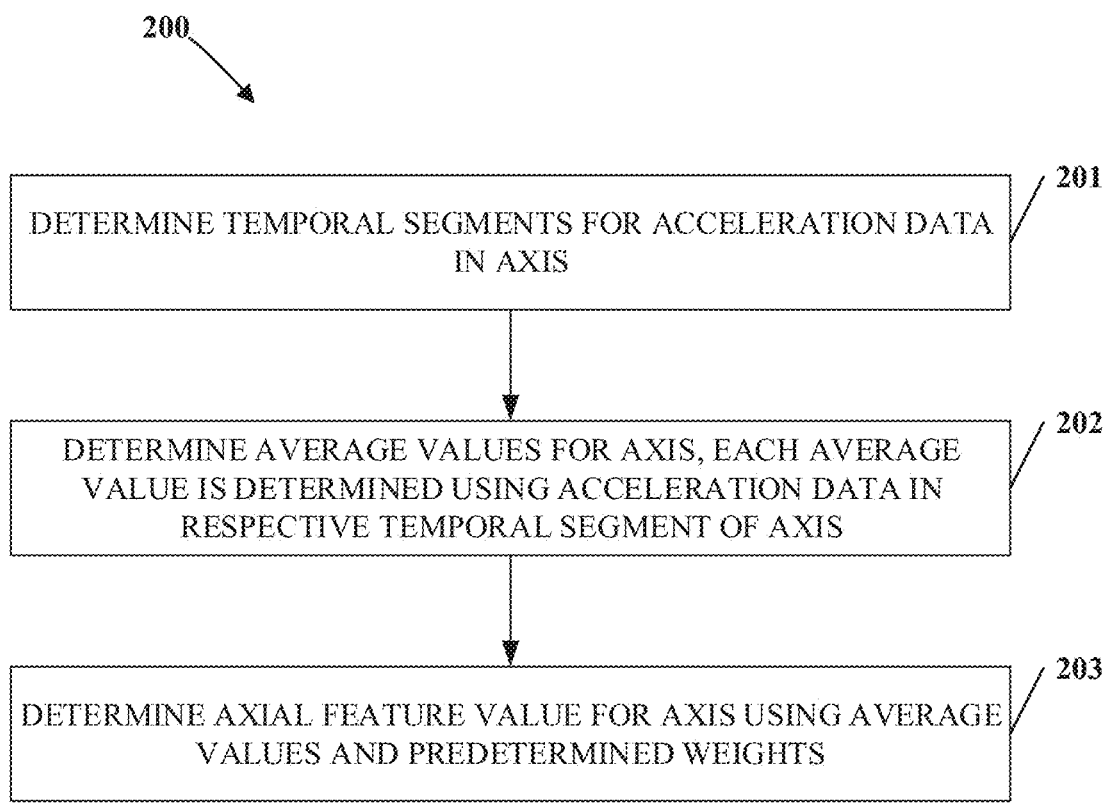
FIG. 2 is a flowchart of an example process of a method for obtaining an axial feature value according to an implementation of this disclosure.

FIG. 2 is a flowchart of an example process 200 of a method for obtaining an axial feature value according to an implementation of this disclosure. As shown in FIG. 2, the process 200 can include the following operations.

At operation 201, temporal segments for acceleration data in an axis of the multiple axes can be determined. For example, the acceleration data for each axial direction can be separated into M segments by time. M can be a positive integer. For example, for the three-axis accelerometer, acceleration data in x-, y-, and z-direction can be respectively divided into M segments.

At operation 202, average values for the axis are determined. Each average value can be determined using acceleration data in a respective temporal segment of the axis. For example, for acceleration data of each segment of the M segments, the average value (e.g., a median value or a mean value) is determined to obtain a mean-value vector having a length M in the set time period. To ease explanation without causing any confusion or ambiguity, the "mean value" is used as examples for the average values in the description herein. It should be understand that, the "mean value" can be replaced by a "medial value," a "middle value," a "weighted mean value," or any other suitable averaged value for various implementations.

At operation 203, an axial feature value for the axis is determined using the average values and the predetermined weights. For example, for the mean-value vector, a difference vector can be determined, and a weighted sum of elements of the difference vector can be determined using the predetermined weights to obtain an axial feature value for each axial direction. The difference vector can have a length M−1. The mean-value vector, the difference vector, the axial feature value, and the predetermined weights are described as follows.

In an implementation, for each of the x-, y- and z-axis of the three-axis accelerometer, 1500 acceleration data points can be received per minute. To ease the explanation without causing any ambiguity, the x-axis is described as an example hereinafter. The 1500 acceleration data points of the x-axis can be divided into 10 segments (i.e., M=10), with each segment having 150 acceleration data points.

A mean value can be determined for the 150 acceleration data points in each segment of the acceleration data in the x-axis. The resulted mean-value vector can be expressed as:

$mean_x=[x_1,x_2,\ldots,x_{10}]$ wherein $x_1, x_2, x_3, \ldots, x_{10}$ represent the mean of the 150 acceleration data points in each segment, respectively. For example, the mean value in each segment can be determined by averaging a sum of the 150 acceleration data points. Although arithmetic mean values are used as examples herein, this disclosure is not limited to any specific type of mean values. For example, geometric mean values, harmonic mean values, weighted mean values, or any other type of mean values can be used. Similarly, mean-value vectors for the y- and z-axis can be obtained and expressed as:

$mean_y=[y_1,y_2,\ldots,y_{10}]$ $mean_z=[z_1,z_2,\ldots,z_{10}]$

A difference vector of the mean-value vectors can be determined. For example, a mean of a segment of the acceleration data can be subtracted from a mean of a preceding segment of the acceleration data to obtain the difference vector that can be expressed as:

$diff_x=[x_2-x_1,x_3-x_2,\ldots,x_{10}-x_9]$

Similarly, mean-value vectors for y-axis and z-axis can be expressed as:

$diff_y=[y_2-y_1,y_3-y_2,\ldots,y_{10}-y_9]$ $diff_z=[z_2-z_1,z_3-z_2,\ldots,z_{10}-z_9]$ The difference vectors can be added in cumulation. Take the x-axis as an example, a cumulative sum can be determined as:

$$cumsum_{diff_x}(k) = \sum_{i=1}^{k} (x_{i+1} - x_i), k = 1, 2, \ldots, M-1$$

In this example, M=10 and $cumsum_{diff_x}(k)$ can include 9 different sums. For each value of k, the cumulative sum is determined by adding elements of the difference vector from the first element up to the k-th element.

Similarly, cumulative sums for y-axis and z-axis can be determined as:

$$cumsum_{diff_y}(k) = \sum_{i=1}^{k} (y_{i+1} - y_i), k = 1, 2, \ldots, M-1$$

$$cumsum_{diff_z}(k) = \sum_{i=1}^{k} (z_{i+1} - z_i), k = 1, 2, \ldots, M-1$$

Different predetermined weights (e.g., weight coefficients w) can be assigned to the above cumulative sums $cumsum_{diff_x}(k)$, $cumsum_{diff_y}(k)$, and $cumsum_{diff_z}(k)$, to obtain axial feature values $sum_{weighted_x}$, $sum_{weighted_y}$, and $sum_{weighted_z}$ for the x-, y-, and z-axis, respectively:

$$sum_{weighted_x} = \sum_{j=1}^{d} w_j \cdot cumsum_{diff_x}(j)$$

$$sum_{weighted_y} = \sum_{j=1}^{d} w_j \cdot cumsum_{diff_y}(j)$$

$$sum_{weighted_z} = \sum_{j=1}^{d} w_j \cdot cumsum_{diff_z}(j)$$

Wherein d is a parameter indicative of the total number of the weight coefficients, and the weight coefficients $w_j$ can be predetermined by collecting and statistically analyzing user habits (e.g., multi-axial acceleration data received by the wearable device or derived data) in an initial or predetermined time period (e.g., the first month) of using the wearable device.

The mean values of the segments of the acceleration data can better represent user performance under the microactivity state. The difference vectors of the mean-value vectors can represent a difference between two consecutive sampling points. For example, when the difference is sufficiently small (e.g., less than a preset threshold value), values of a difference vector can be close to zero. In this way, by obtaining the axial feature values after determining the weighted sums for the difference vectors of the mean-value vectors, the microactivity state of the user in the time period can be relatively accurately determined. Therefore, the microactivity states of the user can be better monitored using the axial feature values.

Figure 3A:
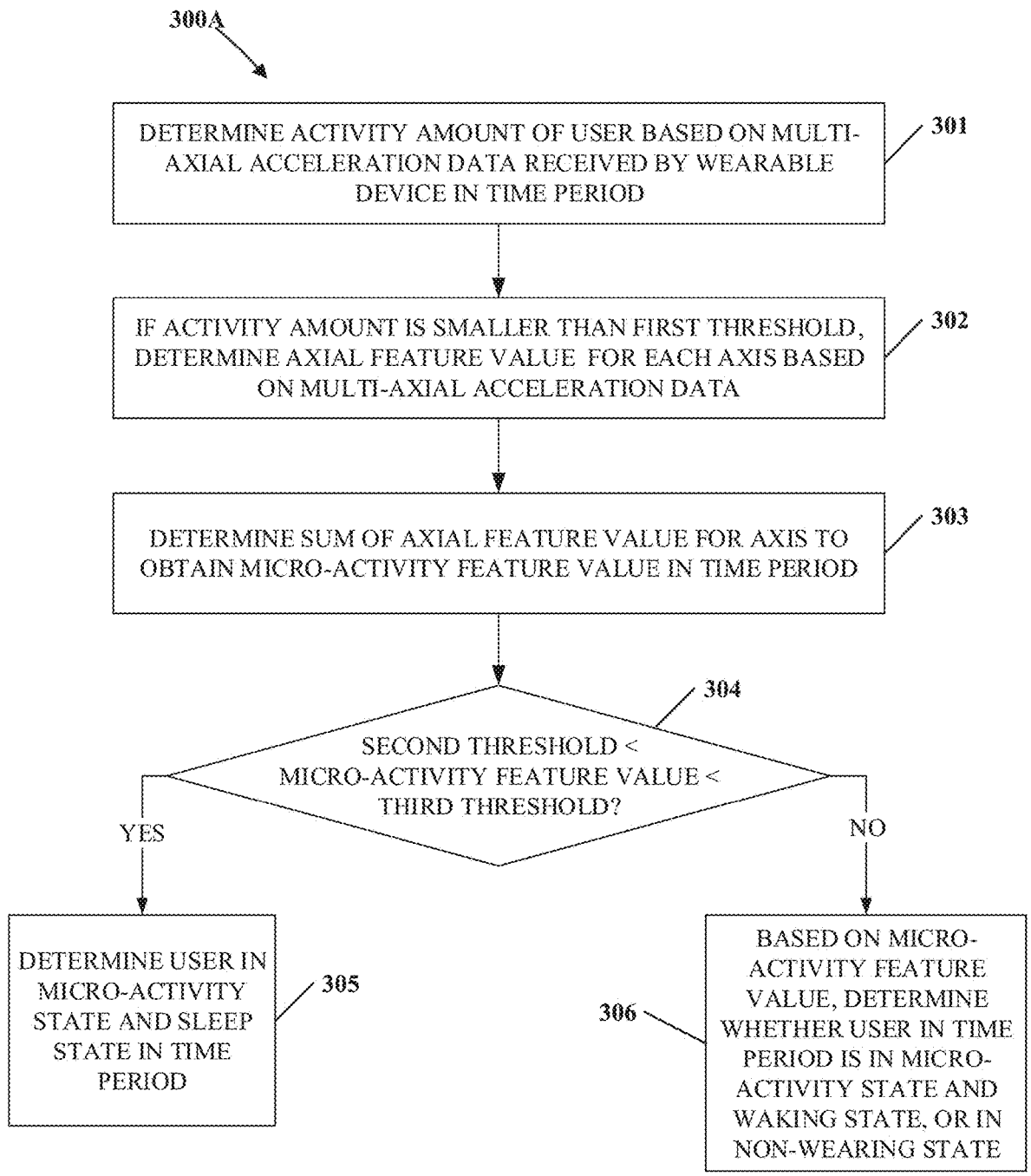
FIG. 3A is a flowchart of an example process of a method for monitoring a microactivity state according to an implementation of this disclosure.
Figure 3B:
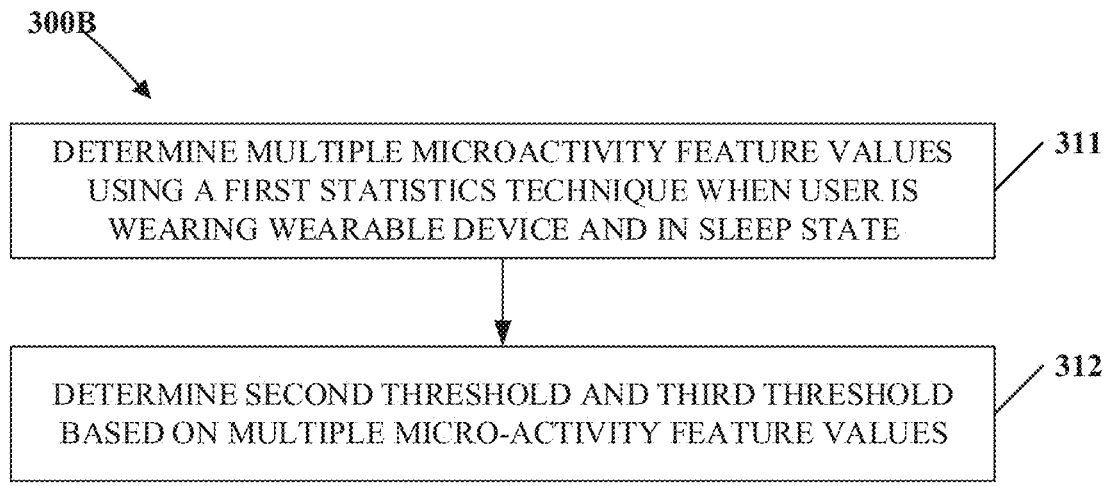
FIG. 3B is a flowchart of an example process of a method for determining a second preset threshold according to an implementation of this disclosure.

FIG. 3A is a flowchart of an example process 300A of a method for monitoring a microactivity state according to an implementation of this disclosure. FIG. 3B is a flowchart of an example process 300B of a method for determining a second preset threshold according to an implementation of this disclosure. As shown in FIG. 3A, the process 300A for monitoring the microactivity state can include the following operations.

At operation 301, an activity amount of a user is determined based on multi-axial acceleration data received in a set time period.

At operation 302, if the activity amount is smaller than a first preset threshold, for each axial direction of the multiple axial directions, an axial feature value is determined based on the multi-axial acceleration data. The first preset threshold can be a positive number greater than zero.

Related details for the operations 301 and 302 can be similar to the description in FIG. 1A or FIG. 2, and will not be repeated in detail here.

At operation 303, a sum is determined using the axial feature values to obtain a microactivity feature value in the set time period.

In an implementation, the microactivity feature value can be determined by summing the above-determined axial feature values of the x-, y-, and z-axis:

$$\text{sum}_{weighted_{xyz}} = \text{sum}_{weighted_x} + \text{sum}_{weighted_y} + \text{sum}_{weighted_z}$$

At operation 304, it is determined whether the microactivity feature value is greater than a second preset threshold and smaller than a third preset threshold. The third preset threshold can be greater than the second preset threshold.

In an implementation, the second preset threshold and the third preset threshold can be preset and stored in the wearable device by a wearable device provider. For example, the wearable device provider can perform statistical analysis based on actual usage data from mass users to obtain the second preset threshold and the third preset threshold. In a set time period before the user is using the wearable device, the second preset threshold and the third preset threshold can be updated by the process 300B shown in FIG. 3B, to ensure that the microactivity states can be better distinguished based on the second preset threshold and the third preset threshold.

At operation 305, if the microactivity feature value is greater than the second preset threshold and smaller than the third preset threshold, the user is determined as in a microactivity state and a sleep state in the set time period.

As shown in FIG. 1E, label 21 denotes microactivity feature values for the user in the waking state, label 22 denotes microactivity feature values for the user in the sleep state, and label 23 denotes microactivity feature values for the user in the non-wearing state. As can be seen from FIG. 1E, a range can be set based on a second preset threshold 31 and a third preset threshold 32. The second preset threshold 31 is shown as a dotted line below the range and the third preset threshold 32 is shown as a dotted line above the range. When a microactivity feature value is in the range limited by the second preset threshold 31 and the third preset threshold 32, the microactivity state of the user in the set time period can be determined as a microactivity state under a sleep state.

At operation 306, if the microactivity feature value is smaller than the second preset threshold or greater than the third preset threshold, based on the microactivity feature value, it is determined whether the user in the set time period is in the microactivity state and the waking state, or in the non-wearing state.

As shown in FIG. 1E, when a microactivity feature value is greater than the third preset threshold 32 (e.g., the microactivity feature values indicated by label 21), the user can be determined as in the waking state. In addition, when a microactivity feature value is lower than the second preset threshold 31 (e.g., the microactivity feature values indicated by label 23), the user can be determined as in the non-wearing state.

To make usage habits of the user better represented by the second preset threshold and the third preset threshold, the second preset threshold and the third preset threshold can be updated according to the usage data of the user. As shown in FIG. 3B, the updating process 300B can include the following operations.

At operation 311, multiple microactivity feature values are determined using a first statistics technique when the user is wearing the wearable device and in the sleep state. For example, statistics of the microactivity feature values is determined when the user is wearing the wearable device and in the sleep state in the set time period.

At operation 312, the second preset threshold and the third preset threshold are determined based on the statistics of the microactivity feature values.

In an implementation, for a set time period (e.g., a month) starting from a time point when the user is registering a corresponding application for the wearable device, the statistics can be determined and analyzed for the microactivity feature values of the user under the waking state, the non-wearing state, and the sleep state, to determine thresholds that can distinguish those three states. The thresholds can be updated to the wearable device.

The microactivity feature values in different states can have relatively large differences, by using the second preset threshold and the third preset threshold, it can be accurately distinguished whether the user is using the wearable device, in a waking state, or in a sleep state. Therefore, microactivities when the user is in the non-wearing state or the waking state can avoid to be collected into the statistics of the sleep state of the user, and accuracy of monitoring the sleep status can be increased. In addition, by obtaining the second preset threshold and the third preset threshold based on the usage data statistics of the user, the second preset threshold and the third preset threshold can be updated to match usage habits for different users, and the microactivity states of the different users can be better distinguished based on the second preset threshold and the third preset threshold. For example, when a different user is wearing the wearable device, the second threshold and the third threshold can be updated based on the multiple microactivity feature values determined using a second statistics technique. The second statistics technique can be the same as the first statistics technique. The second statistics technique can also be different from the first statistics technique.

Figure 4B:
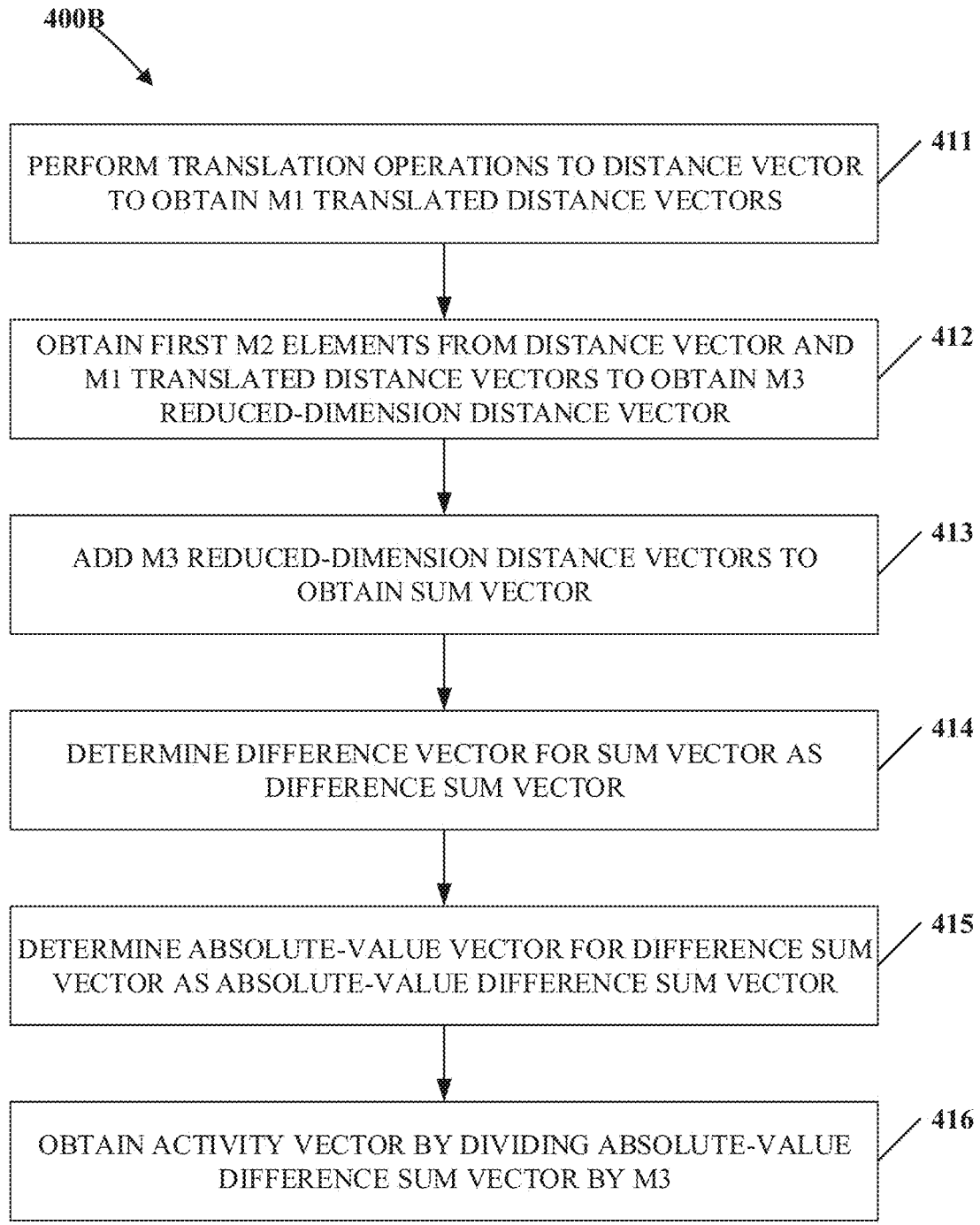
FIG. 4B is a flowchart of an example process of operation 402 shown in FIG. 4A according to an implementation of this disclosure.
Figure 4C:
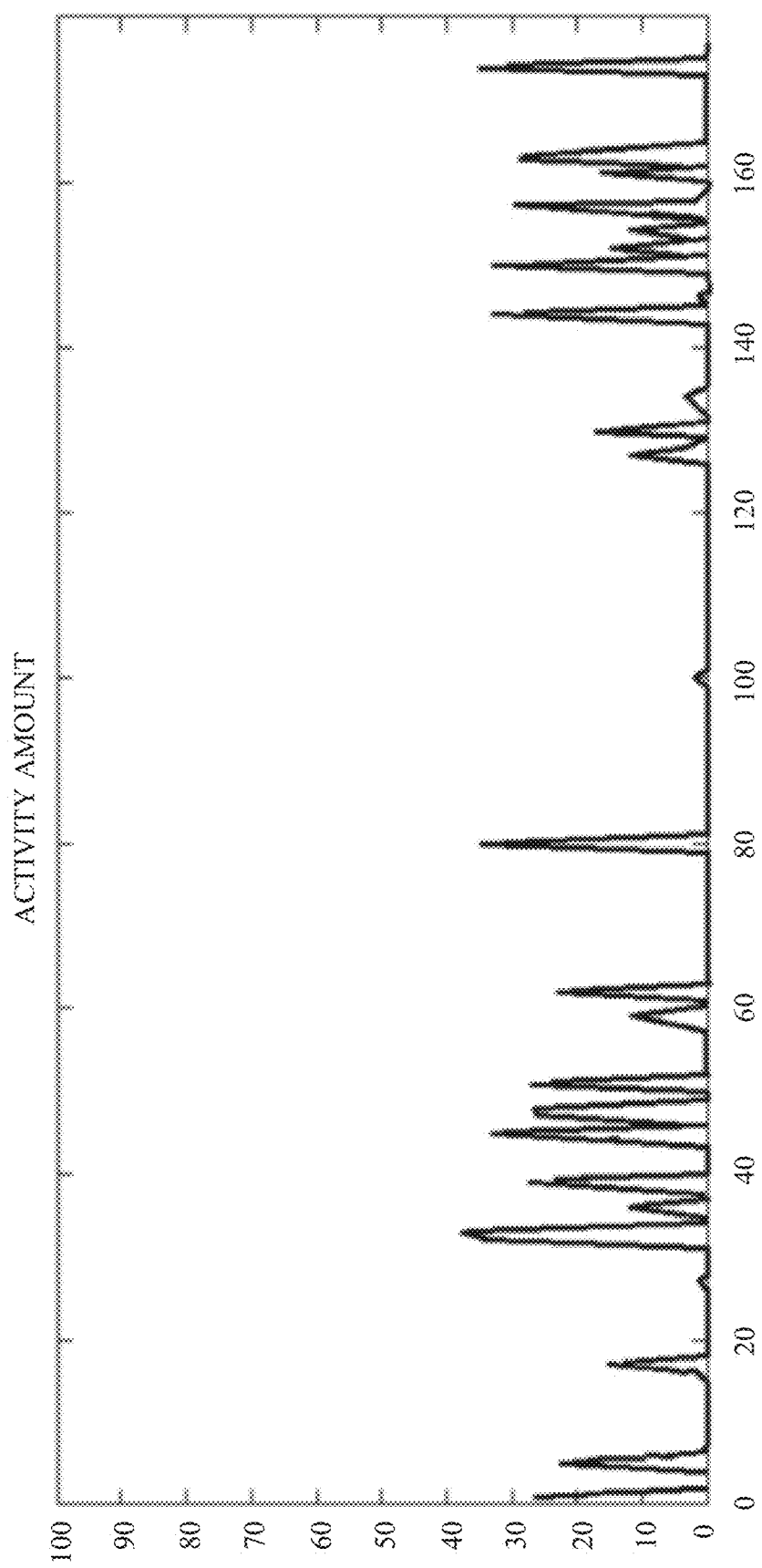
FIG. 4C is a diagram of example activity amounts of a user.

FIG. 4A is a flowchart of an example process 400A of a method for determining an activity amount of a user according to an implementation of this disclosure. FIG. 4B is a flowchart of an example process 400B of operation 402 shown in FIG. 4A according to an implementation of this disclosure. FIG. 4C is a diagram of example activity amounts of a user. As shown in FIG. 4A, the process 400A for determining the activity amount of the user includes the following operations.

At operation 401, distance sets are determined. For each axis of the multiple axes, a distance set (e.g., a distance vector) can include multiple distances (e.g., Euclidean distances) determined using acceleration data in the axis. For example, Euclidean distances can be determined for acceleration data of multiple axial directions to obtain a distance vector in a set time period. The Euclidean distance can be determined between a reference point and a spatial point of an accelerometer, in which the spatial point can be determined using the acceleration data.

For example, the Euclidean distance can be determined using acceleration data received by a three-axis accelerometer. For each of x-, y-, and z-axis of the three-axis accelerometer, 1500 acceleration data points can be received in one minute. A spatial point (x, y, z) of the three-axis accelerometer can be determined for each acceleration data point, and a Euclidean distance s can be determined between the (x, y, z) and the reference point, such as, for example, (0, 0, 0). The distance vector can be express as:

$$S=[s_1,s_2,\ldots,s_N]$$

wherein N is a quantity of sampling points in the set time period. In this example, N=1500.

At operation 402, an activity vector indicative of an activity amount of a user is determined based on the distance vector.

In an implementation, the activity vector can be obtained by translating elements of the distance vector in a tail-to-head manner. For example, the activity vector can be expressed as:

$$new_s=[new_{s1},new_{s2},new_{s3},new_{s4}]$$

Description of the activity vector will be detailed in FIG. 4C and will not be described in detail here.

At operation 403, an activity amount of the user is determined using the activity vector. For example, the activity vector can be summed, squared and divided by 2 to obtain the activity amount based on the user activity vector represented as:

$$(new_{s1}+new_{s2}+new_{s3}+new_{s4})^2/2$$

The activity amount of the user in the set time period can be determined as above. As shown in FIG. 4C, the horizontal axis for activity amount indicates time in a unit of minute. The vertical axis indicates magnitude values of the activity amount. For time periods with the activity amount being or around zero, the user can be in a waking state, a non-wearing state, or a sleep state. Therefore, states corresponding to the activity amount being or around 0 can be accurately distinguished in accordance with the processes described in FIG. 1A or FIG. 3B.

As shown in FIG. 4B, the operation 402 can be implemented by the process 400B.

At operation 411, translation operations are performed to the distance vector to obtain M1 translated distance vectors. M1 is a first set number and can be an integer greater than one.

In an implementation, the translation operations for the distance vector $s=[s_1, s_2, \ldots, s_N]$ can include translating or "rotating" elements of s to the left one by one. For example, by translating the distance vector $s=[s_1, s_2, \ldots, s_N]$ to the left by 1, a distance vector $s1=[s_2, \ldots, s_N, s_1]$ can be obtained. By translating the distance vector s1 to the left by 1, a distance vector $s2=[s_3, \ldots, s_N, s_1, s_2]$ can be obtained. By translating the distance vector s2 to the left by 1, a distance vector $s3=[s_4, \ldots, s_N, s_1, s_2, s_3]$ can be obtained. In this implementation, the first set number M1 can be 3.

At operation 412, for each of the distance vector and the M1 translated distance vectors, first M2 elements are extracted to obtain M3 reduced-dimension distance vectors. M2 is a second set number, and M3 is a third set number. The third set number M3 can be the first set number M1 increased by one.

In an implementation, for an N-dimension distance vector s and three N-dimension translated distance vectors s1, s2, and s3, N−3 dimensional (i.e., the dimension of N is reduced by 3) data can be extracted, respectively, to obtain four N−3 dimensional reduced-dimension distance vectors, which can be expressed as:

$$new_{s1}=[s_1,s_2,\ldots,s_{N-3}]$$

$$new_{s2}=[s_2,s_3,\ldots,s_{N-2}]$$

$$new_{s3}=[s_3,s_4,\ldots,s_{N-1}]$$

$$new_{s4}=[s_4,s_5,\ldots,s_N]$$

In this implementation, the second set number M2 is N−3, and the third set number M3 is 4. It should be understood that specific values of the first set number, the second set number, and the third set number can be arbitrarily set according to actual application scenarios, and are not limited to the above examples.

At operation 413, a sum of the M3 reduced-dimension distance vectors is determined to obtain a sum vector.

For example, by adding the four N−3 dimensional reduced-dimension distance vectors, the sum vector can be obtained as:

$$new_s=new_{s1}+new_{s2}+new_{s3}+new_{s4}$$

At operation 414, a difference vector of the sum vector (referred to as a "difference sum vector") is determined based on the sum vector.

At operation 415, an absolute-value vector for the difference sum vector (referred to as an "absolute-value difference sum vector") is determined based on the difference sum vector.

In an implementation, the determination of the difference sum vector using the sum vector can be similar to the determination of the difference vector using the mean-value vectors, which will not be detailed here. The absolute-value difference sum vector can be obtained by determining an absolute value for each element of the difference sum vector.

At operation 416, an activity vector is determined by dividing the absolute-value difference sum vector by the third set number M3.

In an implementation, the activity vector can be obtained by dividing the absolute-value difference sum vector by 4 (i.e., M3=4).

In this implementation, based on received multi-axial acceleration data, an activity vector indicative of an activity amount of microactivities of a user can be obtained, which can make analysis of the activity amount of the microactivities more complete and objective.

It should be understood that the above description is just examples for monitoring the activity amount of the user based on the acceleration data received from a three-axis accelerometer. The activity amount can also be determined from acceleration data received from accelerometer with more axes or two axes. In addition, when determining the activity amount, the used processing orders of the Euclidean distances, the translation operations, the difference operations, the summation operations, and the averaging operations are not limited to the aforementioned examples. In addition, when determining the microactivity feature values, the used processing orders of the mean values, the differences, the cumulative sums, and the weights are not limited to the aforementioned examples. As long as the activity amount and the microactivity feature values can be determined, any the aforementioned operations can be exchanged, replaced, combined, separated, added, or removed.

Figure 5:
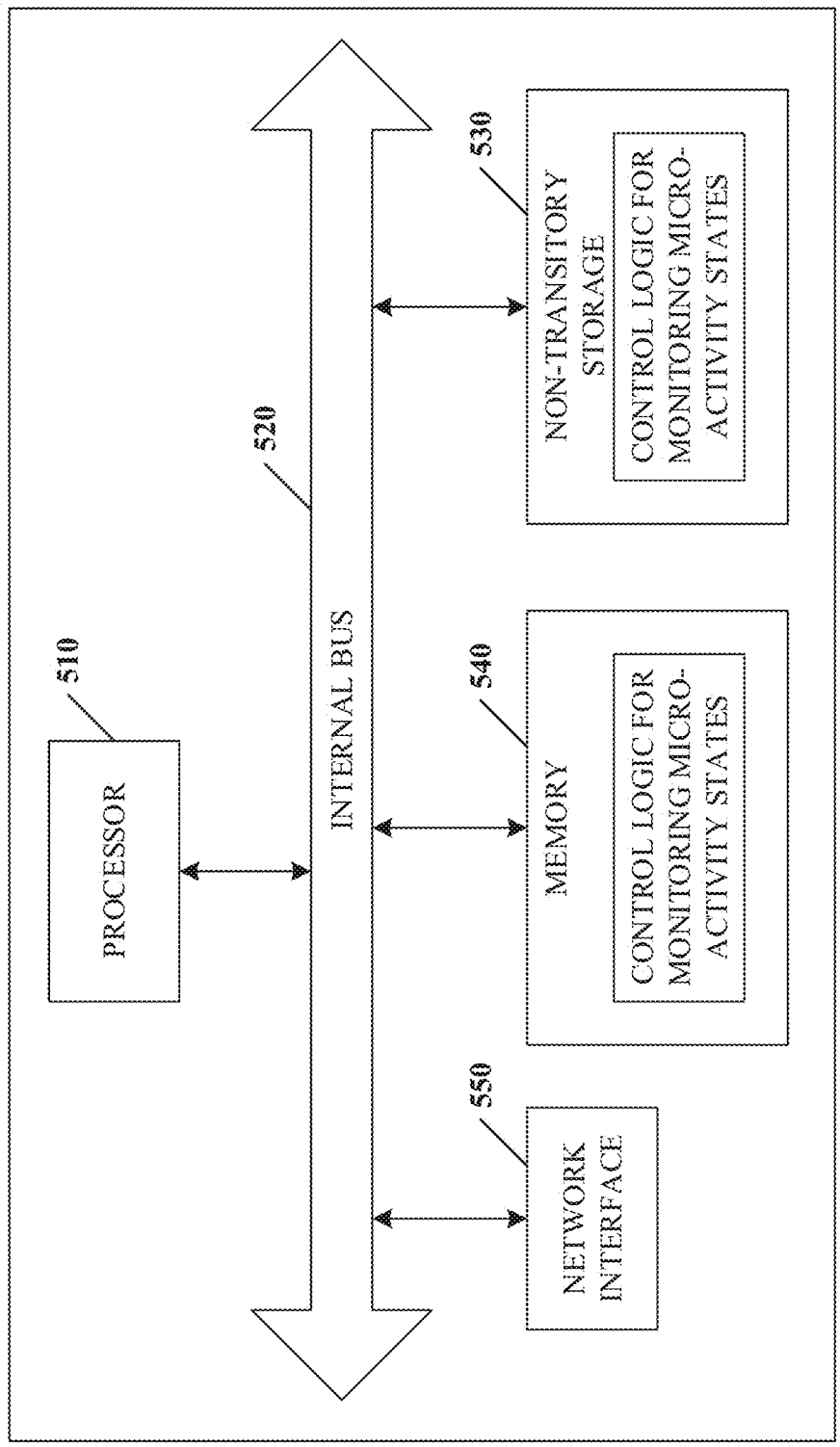
FIG. 5 is a diagram of example structures of a wearable device according to an implementation of this disclosure.

To implement the above-described method of monitoring microactivity states, an apparatus (e.g. a wearable device) is disclosed according to an implementation of this disclosure. As shown in FIG. 5, the hardware of the apparatus can include a processor 510, an internal bus 520, a network interface 550, a memory 540, and a non-transitory storage 530. The apparatus can also include hardware for other functions or services, such as, for example, multi-axial accelerometers for collecting multi-axial acceleration data.

The processor 510 can be any type of device, or multiple devices, capable of manipulating or processing information. The processor 510 can be any type of device, or multiple devices, capable of manipulating or processing information. The processor 510 can include a central processor (e.g., a central processing unit or CPU). The processor 510 can also include a graphics processor (e.g., a graphics processing unit or GPU). Although the examples herein can be practiced with a single processor 510 as shown, advantages in speed and efficiency can be achieved using more than one processor. The processor 510 can be distributed across multiple machines or devices (each machine or device having one or more processors) that can be coupled directly or across a local area or other network.

The memory 540 herein can be any device, or multiple devices, capable of storing codes and data that can be accessed by the processor 510 (e.g., via the internal bus 520). Although a single bus is shown in FIG. 5, multiple buses can be utilized. For example, the memory herein can be a random access memory (RAM), a read-only memory (ROM), an optical/magnetic disc, a hard drive, a solid state drive, a flash drive, a security digital (SD) card, a memory stick, a compact flash (CF) card, or any combination of any suitable type of storage device. The codes can include an operating system (OS) and one or more application programs (e.g., apps) processing and/or outputting the data. The memory herein can be distributed across multiple machines or devices, such as a network-based memory or cloud-based memory.

The network interface 550 can be implemented in various ways, such as a transponder/transceiver device, a modem, a router, a gateway, a circuit, a chip, a wired network adapter, a wireless network adapter, a Bluetooth adapter, an infrared adapter, an NFC adapter, a cellular network chip, or any suitable type of device in any combination that is coupled to the processor 510 using the internal bus 520 to provide functions of communication with a network.

The non-transitory storage 530 can include any suitable non-transitory computer readable medium, such as a hard disc drive, a memory device, a solid state drive, a flash drive or an optical drive. The non-transitory storage 530 can provide additional memory when high processing requirements exist. The non-transitory storage 530 can also store any form of data. Further, the non-transitory storage 530 can be a component of hardware configuration or can be a shared device that can be accessed via a network.

For example, the processor 510 can read machine-executable instructions associated with a control logic for monitoring microactivity states from the non-transitory storage 530 to the memory 540, and execute the machine-executable instructions. The control logic can be implemented as software, hardware, or a combination thereof. In addition to software implementations, this disclosure does not exclude implementations by other means, such as, for example, logic devices or combinations of hardware and software. Execution entities (e.g., function modules described as follows) for each operation to monitor microactivity states are not limited to the logic units in examples described here, and can be hardware or logic devices.

Figure 6:
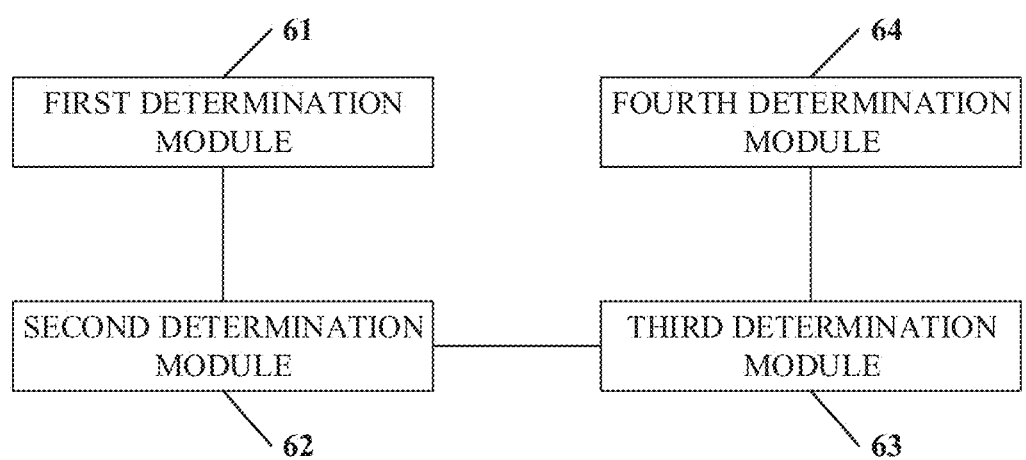
FIG. 6 is a box diagram of an example control logic for monitoring microactivity states according to an implementation of this disclosure.

FIG. 6 is a box diagram of an example control logic for monitoring microactivity states according to an implementation of this disclosure. As shown in FIG. 6, the control logic for monitoring microactivity states can include a first determination module 61, a second determination module 62, a third determination module 63, and a fourth determination module 64. The determination modules 61-64 can be implemented as software, hardware, or a combination thereof. For example, the determination modules 61-64 can be implemented as the machine-executable codes stored in the memory 540 and/or the non-transitory storage 530 that can be executed by the processor 510. For another example, the determination modules 61-64 can be implemented as hardware integrated circuits associated with the apparatus.

The first determination module 61 can be configured to determine an activity amount of a user in a set time period based on multi-axial acceleration data in multiple axial directions received. The second determination module 62 can be configured to determine an axial feature value for each axial direction based on the multi-axial acceleration data if the activity amount determined by the first determination module 61 is smaller than a first preset threshold, For example, the first preset threshold can be a positive number greater than zero. The third determination module 63 can be configured to determine a microactivity feature value for the user in the set time period based on the axial feature value determined for each axial direction by the second determination module 62. The fourth determination module 64 can be configured to determine a microactivity state for the user in the set time period based on the microactivity feature value determined by the third determination module 63.

Figure 7:
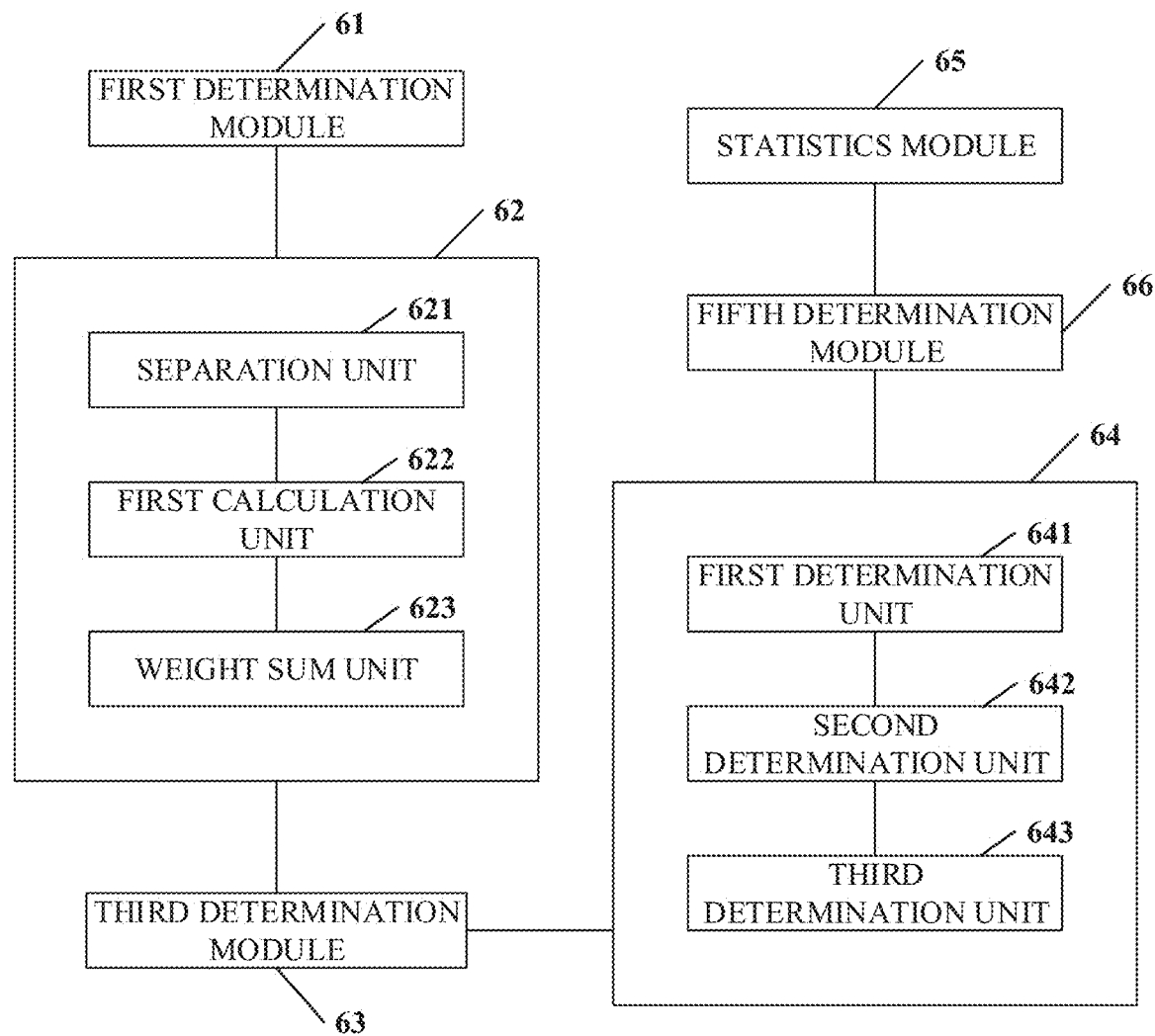
FIG. 7 is a box diagram of an example control logic for monitoring microactivity states according to another implementation of this disclosure.

FIG. 7 is a box diagram of an example control logic for monitoring microactivity states according to another implementation of this disclosure. The modules and units in FIG. 7 can be implemented as software, hardware, or a combination thereof. For example, the modules and units in FIG. 7 can be implemented as the machine-executable codes stored in the memory 540 and/or the non-transitory storage 530 that can be executed by the processor 510. For another example, the modules and units in FIG. 7 can be implemented as hardware integrated circuits associated with the apparatus.

In an implementation, as shown in FIG. 7, the second determination module 62 can include a separation unit 621, a first calculation unit 622, and a weight sum unit 623. The separation unit 621 can be configured to divide or separate acceleration data for each axial direction into M segments. For example, M can be a positive integer. The first calculation unit 622 can be configured to determine a mean or mean value for acceleration data of each segment of the M segments separated by the separation unit 621 to obtain a mean-value or mean-value vector having a length M in the set time period. The weight sum unit 623 can be configured to determine a weighted sum for a difference vector of the mean-value or mean-value vector determined by the first calculation unit 622 to obtain an axial feature value for each axial direction. For example, the difference vector can have a length M−1.

In an implementation, as shown in FIG. 7, the third determination module 63 can be configured to determine a sum using the axial feature value for each axial direction as the microactivity feature value in the set time period.

In an implementation, as shown in FIG. 7, the fourth determination module 64 can include a first determination unit 641, a second determination unit 642, and a third determination unit 643. The first determination unit 641 can be configured to determine whether the microactivity feature value is greater than a second preset threshold and smaller than a third preset threshold. The second determination unit 642 can be configured to determine a microactivity state in which the user is in a sleep state in the set time period if the microactivity feature value is greater than the second preset threshold and smaller than the third preset threshold. The third determination unit 643 can be configured to determine a microactivity state in which the user is in a waking state, or that the user is not wearing the wearable device in the set time period, if the microactivity feature value is greater than the third preset threshold or smaller than the second preset threshold, respectively.

In an implementation, as shown in FIG. 7, the control logic for monitoring microactivity states can further include a statistics module 65 and a fifth determination module 66. The statistic module 65 can be configured to determine, in the set time period, statistics of microactivity feature values when the user is wearing the wearable device and in a sleep state. The fifth determination module 66 can be configured to determine the second preset threshold and the third preset threshold based on the statistics of the microactivity feature values when the user is in the sleep state. The determined second preset threshold and the third preset threshold can be used by the first determination unit 641 to determine whether the microactivity feature value is greater than a second preset threshold and smaller than a third preset threshold.

Figure 8:
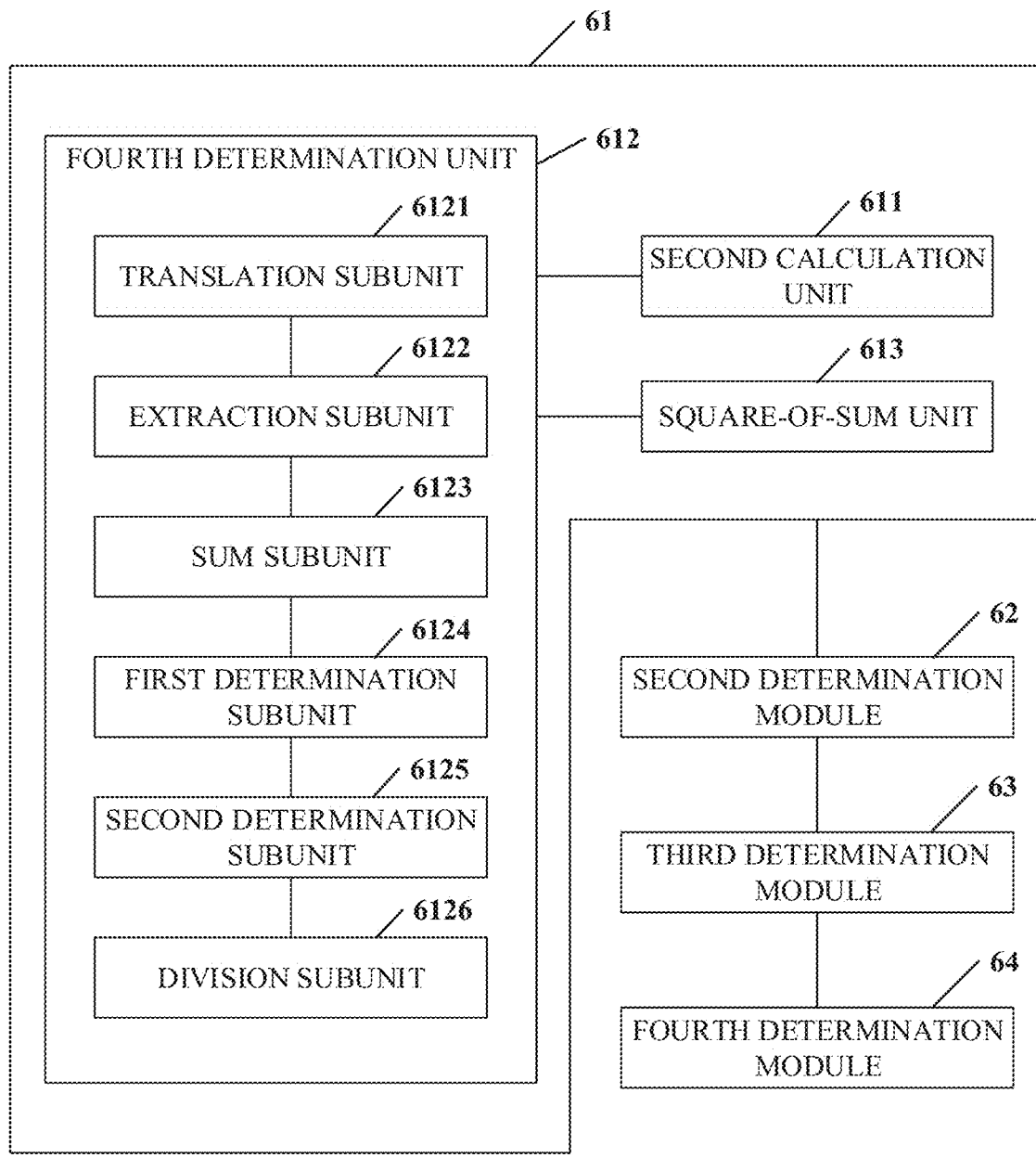
FIG. 8 is a box diagram of another example control logic for monitoring microactivity states according to another implementation of this disclosure.

FIG. 8 is a box diagram of another example control logic for monitoring microactivity states according to another implementation of this disclosure. The modules, units, and subunits in FIG. 8 can be implemented as software, hardware, or a combination thereof. For example, the modules, units, and subunits in FIG. 8 can be implemented as the machine-executable codes stored in the memory 540 and/or the non-transitory storage 530 that can be executed by the processor 510. For another example, the modules, units, and subunits in FIG. 8 can be implemented as hardware integrated circuits associated with the apparatus.

In an implementation, as shown in FIG. 8, the first determination module 61 can include a second calculation unit 611, a fourth determination unit 612, a square-of-sum unit 613. The second calculation unit 611 can be configured to determine a Euclidean distance for acceleration data for each axial direction to obtain a distance vector in the set time period. The fourth determination unit 612 can be configured to determine an activity vector indicative of the activity amount of the user based on the distance vector determined by the second calculation unit 611. The square-of-sum unit 613 can be configured to determine the activity amount of the user by dividing a square of a sum of the activity vector by two.

In an implementation, as shown in FIG. 8, the fourth determination unit 612 can include a translation subunit 6121, an extraction subunit 6122, a sum subunit 6123, a first determination subunit 6124, a second determination subunit 6125, and a division subunit 6126. The translation subunit 6121 can be configured to perform translation operations to the distance vector to obtain a first set number (e.g., M1) of translated distance vectors. For example, the first set number can be an integer greater than one. The extraction subunit 6122 can be configured to extract, for each of the distance vector and the first set number (e.g., M1) of the translated distance vectors, first second set number of elements (e.g., first M2 elements), to obtain a third set number of (e.g., M3) reduced-dimension distance vectors. For example, the third set number can be the first set number increased by one. The sum subunit 6123 can be configured to determine a sum of the third set number of (e.g., M3) reduced-dimension distance vectors to obtain a sum vector. The first determination subunit 6124 can be configured to determine a difference vector for the sum vector as a difference sum vector. The second determination subunit 6125 can be configured to determine an absolute-value vector for the difference sum vector as an absolute-value difference sum vector. The division subunit 6126 can be configured to divide the absolute-value difference sum vector by the third set number (e.g., M3) to obtain the activity vector.

To implement the above-described method for monitoring microactivity states, a wearable device for monitoring sleep of a user is provided according to an implementation of this disclosure. The wearable device can include a multi-axial accelerometer having multiple axes, a processor, and a memory coupled to the processor. The memory can be configured to store instructions which when executed by the processor become operational with the processor to: determine an activity amount of a user based on acceleration data in the multiple axes received by the accelerometer in a time period; based on a determination that the activity amount is smaller than a first threshold, determine a microactivity feature value using the acceleration data and predetermined weights; and determine a microactivity state for the user in the time period based on the microactivity feature value, in which the activity amount of the user is substantially zero in the microactivity state.

When the microactivity feature value is greater than a second threshold and smaller than a third threshold, the user can be determined as in the microactivity state and a sleep state.

When the microactivity feature value is smaller than the second threshold, the user can be determined as not wearing the wearable device.

When the microactivity feature value is greater than the third threshold, the user can be determined as in the microactivity state and a waking state.

In an implementation, the predetermined weights can be determined using acceleration data received by the accelerometer in a predetermined time period and a statistics technique.

In another implementation, the second threshold and the third threshold can be determined based on multiple microactivity feature values determined using a first statistics technique when the user is wearing the wearable device and in the sleep state.

In another implementation, the second threshold and the third threshold can be updated based on multiple microactivity feature values determined using a second statistics technique when a different user is wearing the wearable device. The second statistics technique can be the same as the first statistics technique. The second statistics technique can also be different from the first statistics technique.

In summary, by determining microactivity feature values for a user based on acceleration data and monitoring a microactivity state of the user based on the microactivity feature values, interferences of microactivities of the user before or after sleep can be reduced for monitoring a sleep state of the user. In this way, the sleep state of the user can be monitored more accurately.

As described above, a person skilled in the art should be noted that, all or a portion of aspects of the disclosure described herein can be implemented using a general purpose computer/processor with a computer program that, when executed, carries out any of the respective techniques, algorithms and/or instructions described herein. In addition, or alternatively, for example, a special purpose computer/processor can be utilized which can contain specialized hardware for carrying out any of the techniques, algorithms, or instructions described herein.

The implementations of computing devices as described herein (and the algorithms, methods, instructions, etc., stored thereon and/or executed thereby) can be realized in hardware, software, or any combination thereof. The hardware can include, for example, computers, intellectual property (IP) cores, application-specific integrated circuits (ASICs), programmable logic arrays, optical processors, programmable logic controllers, microcode, microcontrollers, servers, microprocessors, digital signal processors or any other suitable circuit. In the claims, the term "processor" should be understood as encompassing any of the foregoing, either singly or in combination. The terms "signal" and "data" are used interchangeably. Further, portions of the computing devices do not necessarily have to be implemented in the same manner.

The aspects herein can be described in terms of functional block components and various processing operations. The disclosed processes and sequences may be performed alone or in any combination. Functional blocks can be realized by any number of hardware and/or software components that perform the specified functions. For example, the described aspects can employ various integrated circuit components, e.g., memory elements, processing elements, logic elements, look-up tables, and the like, which can carry out a variety of functions under the control of one or more microprocessors or other control devices. Similarly, where the elements of the described aspects are implemented using software programming or software elements the disclosure can be implemented with any programming or scripting language such as C, C++, Java, assembler, or the like, with the various algorithms being implemented with any combination of data structures, objects, processes, routines or other programming elements. Functional aspects can be implemented in algorithms that execute on one or more processors. Furthermore, the aspects of the disclosure could employ any number of conventional techniques for electronics configuration, signal processing and/or control, data processing and the like. The words "mechanism" and "element" are used broadly and are not limited to mechanical or physical implementations or aspects, but can include software routines in conjunction with processors, etc.

Implementations or portions of implementations of the above disclosure can take the form of a computer program product accessible from, for example, a computer-usable or computer-readable medium. A computer-usable or computer-readable medium can be any device that can, for example, tangibly contain, store, communicate, or transport a program or data structure for use by or in connection with any processor. The medium can be, for example, an electronic, magnetic, optical, electromagnetic, or a semiconductor device. Other suitable mediums are also available. Such computer-usable or computer-readable media can be referred to as non-transitory memory or media, and can include RAM or other volatile memory or storage devices that can change over time. A memory of an apparatus described herein, unless otherwise specified, does not have to be physically contained by the apparatus, but is one that can be accessed remotely by the apparatus, and does not have to be contiguous with other memory that might be physically contained by the apparatus.

Any of the individual or combined functions described herein as being performed as examples of the disclosure can be implemented using machine readable instructions in the form of code for operation of any or any combination of the aforementioned computational hardware. Computational code can be implemented in the form of one or more modules by which individual or combined functions can be performed as a computational tool, the input and output data of each module being passed to/from one or more further module during operation of the methods and systems described herein.

The word "example" is used herein to mean serving as an example, instance, or illustration. Any aspect or design described herein as "example" is not necessarily to be construed as preferred or advantageous over other aspects or designs. Rather, use of the word "example" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. In other words, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an aspect" or "one aspect" throughout is not intended to mean the same implementation or aspect unless described as such.

The use of the terms "a" and "an" and "the" and similar referents in the context of describing the disclosure (especially in the context of the following claims) should be construed to cover both the singular and the plural. Furthermore, recitation of ranges of values herein are merely intended to serve as a shorthand method of referring individually to each separate value falling within the range, unless otherwise indicated herein, and each separate value is incorporated into the specification as if it were individually recited herein. Finally, the steps of all methods described herein are performable in any suitable order unless otherwise indicated herein or otherwise clearly contradicted by context. The use of examples, or exemplary language (e.g., "such as") provided herein, is intended merely to better illuminate the disclosure and does not pose a limitation on the scope of the disclosure unless otherwise claimed.

It should be understood that although this disclosure uses terms such as first, second, third, etc., the disclosure should not be limited to these terms. These terms are used only to distinguish similar types of information from each other. For example, without departing from the scope of this disclosure, a first information can also be referred to as a second information; and similarly, a second information can also be referred to as a first information. Depending on the context, the words "if" as used herein can be interpreted as "when," "while," or "in response to."

The implementations described above are only intended as examples and are not intended to limit this disclosure. Any modifications, equivalent substitutions, or improvements in the spirit and principles of this disclosure, are in the scope of this disclosure. As to the device implementations, because they correspond substantially to the disclosed method implementations, description of corresponding parts can be referenced to the method implementations. The device implementations described above are merely illustrative, wherein the units or modules described as separated parts can or cannot be physically separate, and the parts shown as units or modules can or cannot be physical units. They can be in one place, or distributed to multiple networks. Part or all of the modules can be selected accordingly to achieve the object of this disclosure. Anyone with ordinary skill in the art can understand and practice implementations of this disclosure without creative work.

It should be noted that, in this disclosure, relational terms such as first and second are used only to distinguish an entity or an operation from another entity or operation without necessarily requiring or implying that there is any such actual relationship or sequence between these entities or operations. The terms "comprising" or "comprise" or any other variants thereof are intended to encompass a non-exclusive inclusion. For example, processes, methods, devices, or apparatuses comprising a series of elements should include not only those elements, but also other elements not explicitly listed inherent to the processes, methods, devices, or apparatuses. In absence of more limitations, the elements defined by the statement "including a . . . " do not preclude the presence of additional elements in the processes, methods, devices, or apparatuses.

While the disclosure has been described in connection with certain implementations, it is to be understood that the disclosure is not to be limited to the disclosed implementations but, on the contrary, is intended to cover various modifications and equivalent arrangements included in the scope of the appended claims, which scope is to be accorded the broadest interpretation so as to encompass all such modifications and equivalent structures as is permitted under the law.

What is claimed is:

1. A method for monitoring sleep of a user using a wearable device, comprising:
   determining an activity amount of the user based on multi-axial acceleration data received by the wearable device in a time period, wherein the multi-axial acceleration data comprises acceleration data in multiple axes, wherein determining the activity amount comprises:
   obtaining a first distance vector using the multi-axial acceleration data, wherein the first distance vector has a first size M1;
   obtaining second distance vectors from the first distance vector by rotating elements of the first distance vector, wherein obtaining an $n^{th}$ second distance vector of the second distance vectors from the first distance vector comprises rotating n elements of the first distance vector from a head to a tail in the $n^{th}$ second distance vector, and wherein each second distance vector has the first size M1;
   obtaining third distance vectors from the first distance vector and the second distance vectors, wherein obtaining each third distance vector comprises extracting first M2 elements from a respective first distance vector and a second distance vector, wherein M2 is a positive number that is less than the first size M1;
   obtaining an activity vector (AV) using the third distance vectors, wherein the activity vector has a form $AV=[val_1, val_2, \ldots, val_M]$; and
   determining the activity amount from the activity vector as $(val_1+val_{2+} \ldots +val_M)^2/2$;
   based on a determination that the activity amount is smaller than a first threshold, determining a microactivity feature value using the multi-axial acceleration data and predetermined weights; and
   determining a microactivity state for the user in the time period based on the microactivity feature value, wherein the activity amount of the user is substantially zero in the microactivity state.

2. The method of claim 1, further comprising:
   based on a determination that the activity amount is greater than or equal to the first threshold, determining the user is in a non-sleep state.

3. The method of claim 1, wherein determining the microactivity feature value comprises:
   determining axial feature values for the multiple axes, wherein each axial feature value is determined using weighted acceleration data in a respective axis of the multiple axes; and
   determining the microactivity feature value by summing the axial feature values.

4. The method of claim 3, wherein determining the axial feature values for the multiple axes comprises:
   determining temporal segments for acceleration data in an axis of the multiple axes;
   determining average values for the axis, wherein each average value is determined using acceleration data in a respective temporal segment of the axis; and
   determining an axial feature value for the axis using the average values and the predetermined weights.

5. The method of claim 4, further comprising:
   determining the predetermined weights using the multi-axial acceleration data received by the wearable device in a predetermined time period and a statistics technique.

6. The method of claim 1, wherein determining the microactivity state for the user in the time period based on the microactivity feature value comprises:
   determining whether the microactivity feature value is greater than a second threshold and smaller than a third threshold;
   based on a determination that the microactivity feature value is greater than the second threshold and smaller than the third threshold, determining that the user is in the microactivity state and a sleep state in the time period;
   based on a determination that the microactivity feature value is smaller than the second threshold, determining that the user is not wearing the wearable device in the time period; and
   based on a determination that the microactivity feature value is greater than the third threshold, determining that the user is in the microactivity state and a waking state in the time period.

7. The method of claim 6, further comprising:
   determining the second threshold and the third threshold based on multiple microactivity feature values determined using a first statistics technique when the user is wearing the wearable device and in the sleep state.

8. The method of claim 7, further comprising:
updating the second threshold and the third threshold based on multiple microactivity feature values determined using a second statistics technique when a different user is wearing the wearable device.

9. An apparatus for monitoring sleep of a user, comprising:
a processor; and
a memory coupled to the processor, the memory configured to store instructions which when executed by the processor become operational with the processor to:
determine an activity amount of the user based on multi-axial acceleration data received by a wearable device in a time period, wherein the multi-axial acceleration data comprises acceleration data in multiple axes and the apparatus comprises the wearable device, wherein to determine the activity amount comprises to:
obtain a first distance vector using the multi-axial acceleration data;
obtain second distance vectors from the first distance vector by rotating elements of the first distance vector, wherein obtaining an $n^{th}$ second distance vector of the second distance vectors from the first distance vector comprises rotating n elements of the first distance vector from a head to a tail in the $n^{th}$ second distance vector;
obtain an activity vector (AV) using the second distance vectors, wherein the activity vector has a form AV= $[val_1, val_2, \ldots, val_M]$; and
determine the activity amount from the activity vector as $(val_1+val_{2+} \ldots +val_M)^2/2$;
based on a determination that the activity amount is smaller than a first threshold, determine a microactivity feature value using the multi-axial acceleration data and predetermined weights; and
determine a microactivity state for the user in the time period based on the microactivity feature value, wherein the activity amount of the user is substantially zero in the microactivity state.

10. The apparatus of claim 9, wherein the memory further comprises instructions when executed by the processor become operational with the processor to:
based on a determination that the activity amount is greater than or equal to the first threshold, determine the user is in a non-sleep state.

11. The apparatus of claim 9, wherein the instructions operational with the processor to determine the microactivity feature value further comprise instructions to:
determine temporal segments for acceleration data in each axis of the multiple axes;
determine average values for each axis, wherein each average value is determined using acceleration data in a respective temporal segment of the axis;
determine an axial feature value for each axis using the average values and the predetermined weights; and
determine the microactivity feature value by summing axial feature values of the multiple axes.

12. The apparatus of claim 11, wherein the memory further comprises instructions when executed by the processor become operational with the processor to:
determine the predetermined weights using the multi-axial acceleration data received by the wearable device in a predetermined time period and a statistics technique.

13. The apparatus of claim 9, wherein the instructions operational with the processor to determine the microactivity state for the user in the time period based on the microactivity feature value further comprise instructions to:
determine whether the microactivity feature value is greater than a second threshold and smaller than a third threshold;
based on a determination that the microactivity feature value is greater than the second threshold and smaller than the third threshold, determine that the user is in the microactivity state and a sleep state in the time period;
based on a determination that the microactivity feature value is smaller than the second threshold, determine that the user is not wearing the wearable device in the time period; and
based on a determination that the microactivity feature value is greater than the third threshold, determine that the user is in the microactivity state and a waking state in the time period.

14. The apparatus of claim 13, wherein the memory further comprises instructions when executed by the processor become operational with the processor to:
determine the second threshold and the third threshold based on multiple microactivity feature values determined using a first statistics technique when the user is wearing the wearable device and in the sleep state.

15. The apparatus of claim 14, wherein the memory further comprises instructions when executed by the processor become operational with the processor to:
update the second threshold and the third threshold based on multiple microactivity feature values determined using a second statistics technique when a different user is wearing the wearable device.

16. A wearable device for monitoring sleep of a user, comprising:
an accelerometer having multiple axes;
a processor; and
a memory coupled to the processor, the memory configured to store instructions which when executed by the processor become operational with the processor to:
determine an activity amount of the user based on multi-axial acceleration data in the multiple axes received by the accelerometer in a time period, wherein to determine the activity amount comprises to:
obtain a first distance vector using the multi-axial acceleration data, wherein the first distance vector has a first size M1;
obtain second distance vectors from the first distance vector by rotating elements of the first distance vector in a tail-to-head manner, wherein each second distance vector has the first size M1;
obtain third distance vectors from the first distance vector and the second distance vectors, wherein obtaining each third distance vector comprises extracting first M2 elements from a respective first distance vector or a second distance vector, wherein M2 is a positive number that is less than the first size M1;
obtain an activity vector using the third distance vectors; and
determine the activity amount by operations including summing all elements of the activity vector and squaring the sum;
based on a determination that the activity amount is smaller than a first threshold, determine a microactivity feature value using the multi-axial acceleration data and predetermined weights; and determine a microactivity state for the user in the time period based on the microactivity feature value, wherein the activity amount of the user is substantially zero in the microactivity state, and wherein the user is in the microactivity state and a sleep state when the microactivity feature value is greater than a second threshold and smaller than a third threshold, the user is not wearing the wearable device when the microactivity feature value is smaller than the second threshold, and the user is in the microactivity state and a waking state when the microactivity feature value is greater than the third threshold.

17. The wearable device of claim 16, wherein the memory further comprises instructions when executed by the processor become operational with the processor to:

determine the predetermined weights using the multi-axial acceleration data received by the accelerometer in a predetermined time period and a statistics technique.

18. The wearable device of claim 16, wherein the memory further comprises instructions when executed by the processor become operational with the processor to:

determine the second threshold and the third threshold based on multiple microactivity feature values determined using a first statistics technique when the user is wearing the wearable device and in the sleep state; or update the second threshold and the third threshold based on multiple microactivity feature values determined using a second statistics technique when a different user is wearing the wearable device.

* * * * *

UNITED STATES PATENT AND TRADEMARK OFFICE
CERTIFICATE OF CORRECTION

PATENT NO. : 10,624,575 B2
APPLICATION NO. : 15/497623
DATED : April 21, 2020
INVENTOR(S) : Feifei Zhang and Xiaoming Ren Page 1 of 1

It is certified that error appears in the above-identified patent and that said Letters Patent is hereby corrected as shown below:

On the Title Page

Item (63) under Related U.S. Application Data:
Replace "PCT/CT2016/109624" with --PCT/CN2016/109624--

Signed and Sealed this
Twenty-third Day of June, 2020

Andrei Iancu
*Director of the United States Patent and Trademark Office*